US009333504B2

(12) United States Patent
Polaniec et al.

(10) Patent No.: US 9,333,504 B2
(45) Date of Patent: May 10, 2016

(54) ACTIVE, MICRO-WELL THERMAL CONTROL SUBSYSTEM

(71) Applicant: Siemens Healthcare Diagnostics Inc., Tarrytown, NY (US)

(72) Inventors: Jim Polaniec, Avon, OH (US); David J. Lapeus, Medina, OH (US); Tim Greszler, Oberlin, OH (US); Frank Klingshirn, Medina, OH (US); Chris Sturges, Amherst, OH (US); Matt Schmidt, Strongsville, OH (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/510,436

(22) Filed: Oct. 9, 2014

(65) Prior Publication Data

US 2015/0020532 A1 Jan. 22, 2015

Related U.S. Application Data

(62) Division of application No. 12/077,193, filed on Mar. 17, 2008, now Pat. No. 8,865,457.

(60) Provisional application No. 60/918,190, filed on Mar. 15, 2007.

(51) Int. Cl.

*C12Q 1/00* (2006.01)
*B01L 7/00* (2006.01)
*F25B 21/04* (2006.01)

(52) U.S. Cl.

CPC . *B01L 7/52* (2013.01); *F25B 21/04* (2013.01); *B01L 2200/147* (2013.01); *B01L 2300/0829* (2013.01); *B01L 2300/185* (2013.01); *B01L 2300/1822* (2013.01); *B01L 2300/1844* (2013.01)

(58) Field of Classification Search

CPC ................ B01L 7/52; B01L 2200/147; B01L 2300/0829; B01L 2300/1822; B01L 2300/1844; B01L 2300/185; A61L 2/04; A61L 2/07; A61L 2/0023; A61L 2/06; A61L 3/04; A61L 2/24; B01J 2208/00548; B01J 19/0006; B01J 2219/00094; B01J 8/0285

USPC ........................................................... 422/38

See application file for complete search history.

(56) References Cited

U.S. PATENT DOCUMENTS

| | | | |
|---|---|---|---|
| 5,602,756 | A | 2/1997 | Atwood et al. |
| 5,939,312 | A | 8/1999 | Baier et al. |
| 6,153,426 | A | 11/2000 | Heimberg |
| 6,306,658 | B1 | 10/2001 | Turner et al. |
| 6,556,940 | B1 | 4/2003 | Tretiakov et al. |
| 7,060,948 | B2 | 6/2006 | Cho et al. |
| 2002/0072112 | A1 | 6/2002 | Atwood et al. |
| 2002/0100582 | A1 | 8/2002 | Oldenburg |
| 2004/0223885 | A1 | 11/2004 | Keen et al. |
| 2004/0258568 | A1 | 12/2004 | Lurz et al. |

*Primary Examiner* — Michael Hobbs

(57) ABSTRACT

Devices and systems for active thermal control of sample holding devices for bDNA testing, polymerase chain reaction testing, chemiluminescent immuno-assay testing, and so forth. The thermal control subsystem includes a fluidic circuit, first and second heater assemblies, a centrifugal pump, and a heat exchange device. The first and second heater assemblies include a heat removal device and a controllable thermo-electric device. One or both of the heater assemblies can include a heat spreader. A controller actively controls the pump, the heat removal device, and the thermo-electric devices, to thermally-control sample-containing vessels retained in the holding device.

9 Claims, 2 Drawing Sheets

ACTIVE, MICRO-WELL THERMAL CONTROL SUBSYSTEM

CROSS REFERENCE TO RELATED APPLICATIONS

This is a divisional application claiming priority from U.S. Ser. No. 12/077,193 (now U.S. Pat. No. 8,865,457) filed Mar. 17, 2008 which claims priority to U.S. Provisional Patent Application No. 60/918,190 filed on Mar. 15, 2007, both of which are incorporated by reference herein in their entirety.

STATEMENT REGARDING FEDERALLY SPONSORED RESEARCH OR DEVELOPMENT (Not Applicable)

BACKGROUND OF THE INVENTION

The present invention relates to devices and systems for providing active thermal control of sample-containing assay trays and, more specifically, to devices and systems that provide improved, uniform heat transfer from a sample-containing assay tray using thermo-electric devices, heat spreader plates, and liquid heat exchangers.

Protocols for amplification of RNA or DNA, for example, during polymerase chain reaction (PCR), bDNA, and similar testing, require rapid and uniform heating and cooling of a plurality of sample-containing vessels. Because such testing typically is performed in batches, the rapid and uniform heating and cooling are applied to the plurality of sample-containing vessels simultaneously.

Conventionally, heat transfer for thermo-electric devices and/or heating elements is accomplished by conduction, while cooling of thermal system components is done by convection, or, more conventionally, by air convection. However, thermal performance of such systems is limited by the space needs of relatively large thermal components.

Therefore, it would be desirable to provide a liquid heat-transferring concept that transfers heat by liquid convection rather than by air convection to improve heat transfer and to provide a more compact thermal component size. Thermal control of sensitive reagents used in these protocols is also highly desirable.

SUMMARY OF THE INVENTION

An active thermal control subsystem for controlling the temperature of a sample-containing holding device used in connection with bDNA testing, polymerase chain reaction testing, chemiluminescent immuno-assay testing, and the like is disclosed. The thermal control subsystem includes first and second assemblies, a pump, and a heat exchange device that are fluidly-coupled via a fluidic circuit.

The first and second assemblies include a heat removal device and a thermo-electric device(s). One or more of the first and the second assemblies includes a heat spreader. The heat spreader is further thermally-coupled to the sample-containing holding device, such as a micro-well assay tray. The thermo-electric device(s) is/are disposed between the heat removal device and the heat spreader. Current transmitted to the thermo-electric device(s) is controlled. Depending on the voltage at each junction, heat can be transferred bi-directionally, either from the heat spreader to the heat removal device or from the heat removal device to the heat spreader.

A testing system having active thermal control of a sample-holding device and/or a reagent-containing device is also disclosed. The system includes the thermal control subsystem described above and a controller. The controller controls operation of the pump, the heat exchange device, and the thermo-electric device(s) associated with the first and second assemblies to control the temperature of the sample-holding device and/or reagent-containing device.

Optionally, the system can include a holding device for retaining reagent-containing vessels that is fluidly-coupled to the fluidic system and/or a drain line that is fluidly-coupled to the fluidic system for removing heat-transferring fluid.

BRIEF DESCRIPTION OF THE DRAWINGS

The invention will be better understood by reference to the following more detailed description and accompanying drawings where like reference numbers refer to like parts.

DETAILED DESCRIPTION OF THE INVENTION

U.S. Provisional Patent Application No. 60/918,190 filed on Mar. 15, 2007 and entitled "Active, Micro-well Thermal Control Subsystem", from which priority is claimed, is incorporated herein by reference.

Figure 1:
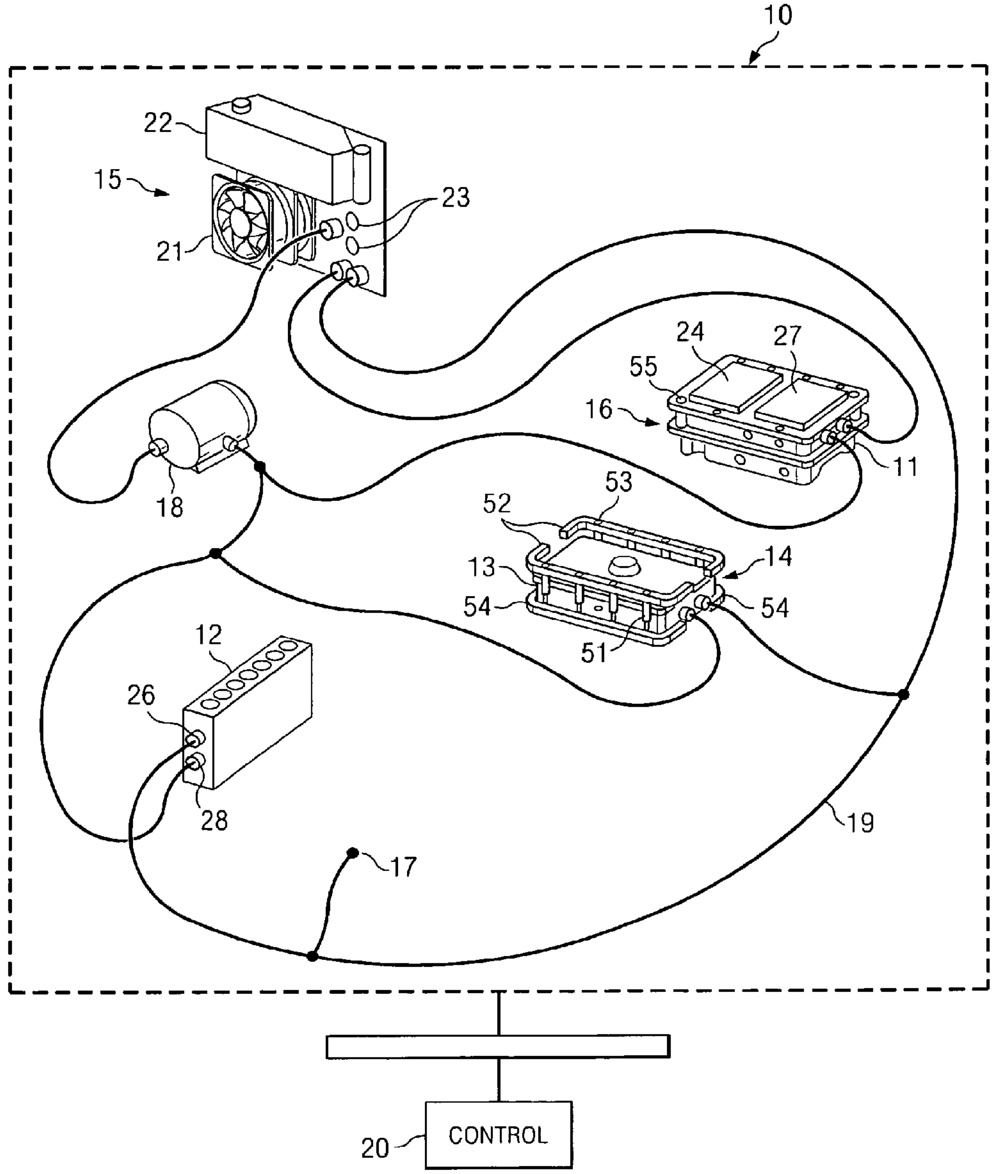
FIG. 1 shows a diagram of a well subsystem in accordance with the present invention.

An active control, micro-well thermal breadboard/micro-well thermal subsystem, e.g., for a bDNA testing system, a chemiluminescent immunoassay system, a PCR testing system, and the like, is disclosed. Referring to FIG. 1, there is shown an active thermal control subsystem 10 for controlling the temperature of at least one micro-well assay tray (not shown). The micro-well assay tray discussed in this disclosure corresponds to a conventional micro-well titer plate for holding multiple, i.e., 96, sample-containing cuvettes. The invention, however, is applicable to other sample-holding devices.

The subsystem 10 is structured and arranged to maintain micro-well plate incubation temperatures between about 20 degrees Centigrade (° C.) and about 70° C., which is to say, between about 68 degrees Fahrenheit (° F.) and 158° F., respectively. Moreover, the subsystem 10 is structured and arranged so that the average temperature of the micro-well assay trays can be maintained within approximately ±0.5° C. of the specified or desired temperature and, moreover, so that the temperature difference between adjacent micro-well assay trays does not exceed approximately ±0.5° C. Optionally, the subsystem 10 of the present invention can also be structured and arranged to control the temperature of sensitive reagents used in the course of the PCR, chemiluminescent or other testing.

The micro-well thermal subsystem 10 of the present invention includes first and second heater trays 14 and 16, a heat exchanger 15, a pump 18, and a fluidic system 19. Optionally, the micro-well thermal subsystem 10 can include a reagent holding device 12 and/or a system controller 20, which in FIG. 1 is shown separate from the micro-well thermal subsystem 10.

Each of the first and second heater trays 14 and 16, the heat exchanger 15, and the reagent holding device 12 are fluidly-coupled via a common fluidic system 19. The fluidic system 19 includes fluid conduits, such as flexible tubing, for circulating a heat-transferring liquid. A drain line 17 can be provided to drain the fluidic system 19 and/or to bleed off excess heat-transferring liquid within the fluidic system 19.

A centrifugal pump 18, such as the RD-05CV24 manufactured by Iwaki Co., Ltd. of Tokyo, Japan, is also fluidly-coupled to the fluidic system 19. The centrifugal pump 18 is adapted to circulate a heat-transferring liquid, such as a water and ethylene-glycol (WEG) mixture, between the first and second heater trays 14 and 16 and the heat exchanger 15, to transfer heat from or transfer heat to the first and second heater trays 14 and 16; between the reagent holding device 12 and the heat exchanger 15, to transfer heat from or transfer heat to the reagent-containing vessels disposed in the reagent holding device 12; and between the fluidic system 19 and a coolant reservoir 25, to add heat-transferring liquid to or to drain heat-transferring liquid from the fluidic system 19.

The reagent holding device 12 of the present invention includes inlet and outlet ports 26 and 28, respectively, and associated internal fluidic connections (not shown) for controlling the temperature of reagent-containing vessels, e.g., test tubes, disposed in the reagent holding device 12. The inlet and outlet ports 26 and 28 are releasably attachable to the external fluidic system 19 for circulating a heat-transferring liquid through the fluidic connections and about the reagent-containing vessels, to control the temperature of the reagent-containing test tubes by liquid convection.

The heat exchanger 15 can be a conventional, radiator-type heat exchanger, having a coolant reservoir 22, a plurality of coils 23, and at least one fan assembly 21. The coolant reservoir is adapted to hold heat-transferring liquid that has been heated in the first or second heater trays 14 and 16 and elsewhere in the fluidic system 19 temporarily. The plurality of coils 23 is adapted to circulate heat-transferring liquid from the coolant reservoir 22 to the fluidic system 19. The fan assembly(ies) 21 is/are adapted to move ambient air against and around the coils 23, to remove heat from the heat-transferring liquid circulating therein. Once sufficient heat has been removed from the heat-transferring liquid circulating in the coils 23, the heat-transferring liquid is re-circulated to the first and second heater trays 14 and 16, to the reagent holding device 12, and/or to the coolant reservoir 22.

Figure 2:
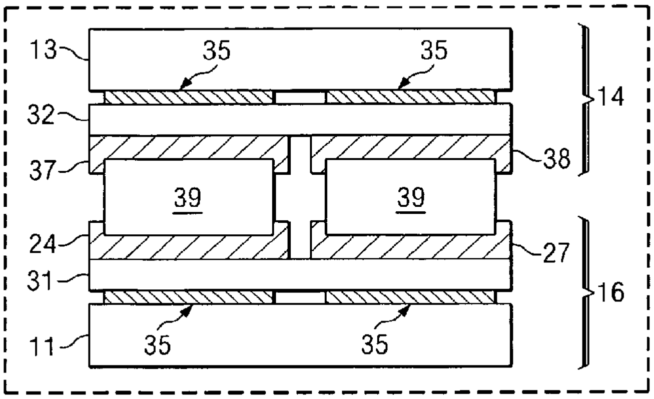
FIG. 2 shows a diagram of micro-well assay trays disposed between first and second heater plates in accordance with the present invention.

Referring to FIG. 2, a first side of each of the first and second heater trays 14 and 16 is operationally- and thermally-coupled to the item(s) being thermally-controlled, e.g., at least one 96-position micro-well assay tray 39. The first side of the second heater tray 16 shown in FIG. 1 and FIG. 2 includes two sub-portions 24 and 27, each of which is adapted for holding a conventional, 96-position micro-well titer plate 39. The first side of the first heater tray 14 includes two sealing pads 37 and 38 that are also adapted, in combination with the associated sub-portions 24 and 27 of the second heater tray 16, for securing the 96-position micro-well titer plates 39 therebetween.

As shown in FIG. 2, the sub-portions 24 and 27 of the second heater plate 16 are thermally-coupled to a heat spreader 31. Optionally (as shown in FIG. 2), the sealing pads 37 and 38 of the first heater tray 14 also can be thermally-coupled to a heat spreader 32. Experimentation by the inventors evinced that micro-well thermal performance is more greatly influenced by the second (lower) heater tray 16 than by the first (upper) heater tray 14. Hence, a heat spreader 32 for the first (upper) heater tray 14 can be omitted to reduce cost and simplify design.

The heat spreaders 31 and 32 are adapted to avoid hot or cold spots within the micro-well assay trays 39, especially during rapid, ramp temperature changes. The heat spreaders 31 and 32 also prevent direct heat transfer from thermo-electric devices (TEDs) 35, which are disposed on the opposite sides of the heat spreaders 31 and 32, to the center of the micro-well assay trays 39.

Heat spreaders 31 and 32 can be manufactured of copper, aluminum or some other relatively-highly thermally-conductive material. More specifically, the heat spreaders 31 and 32 are adapted to ensure that each micro-well assay tray 39 is maintained within approximately ±0.5° C. (±about 1° F.) of the specified temperature; that the temperature difference between adjacent micro-well assay trays 39 does not exceed approximately ±0.5° C.; that the ramp temperature change rate, i.e., "ramping", for heating or cooling the micro-well assay trays 39 is between approximately 1° C./minute (about 2° F.) and approximately 10° C./minute (about 18° F./minute) and, more preferably, between approximately 1° C./minute and approximately 7° C./minute (about 13° F./minute); and that, during ramping, the upper (or lower) target temperature is not exceeded by more than approximately 0.5° C.

As mentioned above, one side of each of the heat spreaders 31 and 32 is operationally- and thermally-coupled to a plurality of thermo-electric devices (TED) 35, which are disposed to be in registration with the sub-portions 24 and 27 and the micro-well assay trays 39. TEDs 35 are thermal controllers that transfer heat across their thickness by the Peltier effect. According to the Peltier effect, applying voltage to the junctions of two dissimilar metals causes a temperature difference between the two junctions. Hence, by varying the polarity of the voltages applied to the junctions, temperatures can be increased or decreased and, more importantly, heat can be transferred from one side of the TED 35 to the other side of the TED 35 in either direction.

Advantageously, heat can be transferred from heat removal devices, i.e., heat sinks 11 and 13, respectively, to the heat spreaders 31 and 32, when ramping up the temperature of the micro-well assay trays 39. Alternatively, heat can be transferred from the heat spreaders 31 and 32 to the heat sinks 11 and 13, respectively, when ramping down the temperature of the micro-well assay trays 39.

Figure 3A:
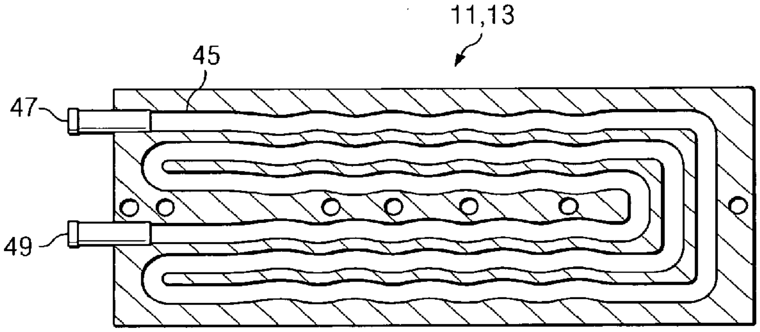
FIG. 3A shows a diagram of a plan view of a heat sink (taken from the bottom) in accordance with the present invention.
Figure 3B:
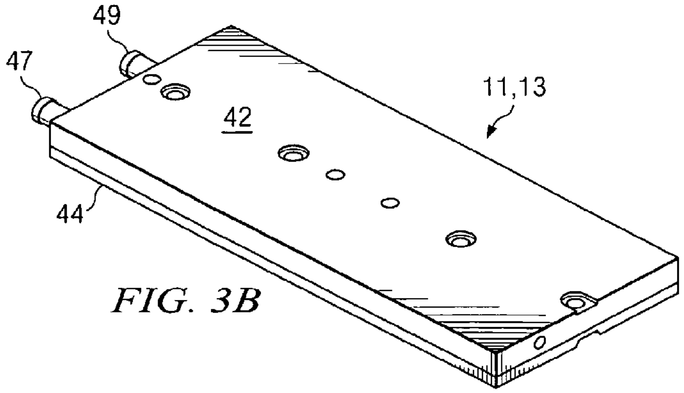
FIG. 3B shows a diagram of an isometric view of the heat sink of FIG. 3A.

Heat sinks 11 and 13 are thermal masses used for removing heat by conduction and/or by convection. Heat sinks 11 and 13 are well known to the art and will not be discussed in great detail. However, referring to FIGS. 3A and 3B, heat sinks 11 and 13 can include two opposing, relatively-highly thermally-conductive plates 42 and 44 that are releasably attachable to one another. At least one fluid-carrying channel 45 is disposed between the two plates 42 and 44. The fluid-carrying channel(s) 45 of the heat sinks 11 and 13 includes an inlet port 49 and an outlet port 47, which are fluidly-coupled to the fluidic system 19.

During operation, the direction of heat transfer between the heat sinks 11 and 13 and the micro-well assay trays 39 depends on whether the TEDs 35 are in a heating or in a cooling mode. During a heating mode, a rapid ramp-up temperature change of the micro-well assay tray(s) 39 is desired. For example, during PCR testing, conventionally, an analyte-containing sample is heated from ambient temperature to about 70° C. (about 158° F.) during the initial de-naturing cycle.

Accordingly, voltages at the junctions of the TEDs 35 are controlled so that heat is transferred from the heat sinks 11 and 13 to the micro-well assay trays 39. More specifically, the heat-transferring liquid in the fluidic system 19 is heated to an elevated temperature (or is allowed to remain at an elevated temperature) sufficient to transfer the necessary heat from the heat-transferring liquid to the heat sink(s) 11 and/or 13. In some instances, the available heat in the heat sink(s) 11 or 13 may be sufficient to rapidly change the temperature of the micro-well assay trays 39 without using a heated liquid to heat the heat sink(s) 11 or 13.

During a cooling mode, a rapid ramp-down temperature change of the micro-well assay tray(s) 39 is desired. Accordingly, voltages at the junctions of the TEDs 35 are controlled so that heat is transferred from the micro-well assay trays 39 to the heat sink(s) 11 and/or 13 via the TEDs 35. Heat-transferring liquid circulating though the channels disposed in the heat sink(s) 11 and/or 13 removes heat from the heat sink(s) 11 and/or 13.

A controller 20 (FIG. 1) is electrically-coupled to the system 10, for the purpose of controlling the centrifugal pump 18, the heat exchanger 15, and each of the TEDs 35 associated with the first and second heater trays 14 and 16. The controller 20 can include electronic hardware, software, and/or applications, driver programs, and other algorithms as well as input/output devices to control the machination of the centrifugal pump 18, the heat exchanger 15, and each of the TEDs 35. More specifically, the controller 20 is adapted to control the temperature of the heat-transferring liquid and, further, to control the heat transfer direction of the TEDs 35, to heat or cool the micro-well assay tray(s) 39 automatically, and in accordance with the protocol of the PCR, bDNA, and related tests.

In one aspect of the present invention, the first heater tray 14 is releasably attachable to the second heater tray 16. Any clamping or other means for temporarily securing the first heater tray 14 to the second heater tray 16 can be used. FIG. 1 shows a fastener-based embodiment, whereby a plurality of fasteners 51, e.g., machine screws, bolts, and the like, are disposed through holes 53 in upper and lower clamping portions 52 and 54, respectively, and, further disposed in associated openings disposed in the second heater tray 16. As the fastening devices 51 are tightened, the upper and lower clamping portions 52 and 54 secure the upper heater tray 14. As the fastening devices 51 are tightened more, the upper and lower heater trays 14 and 16 are tightly secured about the micro-well assay tray(s) 39.

The invention has been described in detail including the preferred embodiments thereof. However, those skilled in the art, upon considering the present disclosure, may make modifications and improvements within the spirit and scope of the invention.

What is claimed is:

1. A method of providing active thermal control of a sample-holding device in a thermal control subsystem, the method comprising:

coupling the sample-holding device to a fluidic circuit;

pumping a heat-transferring fluid through the fluidic circuit for selectively heating or cooling a sample within the sample-holding device under the control of a controller;

thermally-coupling a first assembly, including a controllable first thermo-electric device, a first heat removal device, and a first heat spreader to a first side of said sample-holding device, wherein the first assembly is in a thermal communication with the heat transferring fluid within the fluidic circuit;

thermally-coupling a second assembly, including a controllable second thermo-electric device and a second heat removal device to a second, opposing side of said sample-holding device, wherein the second assembly is in thermal communication with the heat transferring fluid within the fluidic circuit;

at least a some times, removing heat from the heat-transferring fluid in the fluidic circuit using at least one of said first and second heat removal devices and a heat exchanger disposed in the fluidic circuit; and at least at some times selectively controlling at least one of the first and second thermo-electric devices associated with the first and second assemblies to remove heat from, or add heat to, said sample-holding device under the control of the controller.

2. The method as recited in claim 1, wherein controlling the first and second thermo-electric devices associated with the first and second assemblies includes selectively controlling current and voltage polarity to at least one of the thermo-electric devices under the control of the controller, to transfer heat across the at least one of the thermo-electric devices bi-directionally and thereby transfer heat to or remove heat from the sample-holding device.

3. The method of claim 2 wherein the first and second thermo-electric devices comprise peltier effect devices.

4. The method of claim 1 including the step of removing heat from the heat transferring fluid with the heat exchanger within the fluidic circuit, wherein the step of removing heat from the heat transferring fluid with the heat exchanger includes pumping the heat transferring fluid through at least one coil within the heat exchanger and moving ambient air across the at least one coil via at least one fan assembly.

5. The method of claim 1 wherein the thermal control subsystem further includes a reagent-containing device in thermal communication with the heat transferring fluid within the fluidic circuit, the method further including the step of heating a reagent within the reagent-containing device by controlling at least one the first and second thermo-electric devices in thermal communication with the heat transferring fluid within the fluidic circuit to heat the heat transferring fluid and, pumping the heated heat transferring fluid through the fluidic circuit to heat the reagent within the reagent-containing device.

6. The method of claim 1 wherein the thermal control subsystem further includes a reagent-containing device in thermal communication with the fluidic circuit, the method further including the step of cooling a reagent within the reagent-containing device by:

controlling at least one the first and second thermo-electric devices in thermal communication with the heat transferring fluid within the fluidic circuit to cool the heat transferring fluid and, pumping the cooled heat transferring fluid through the fluidic circuit to cool the reagent within the reagent-containing device; or pumping the heat transferring fluid within the fluidic circuit through at least one coil within a heat exchanger and through the reagent-containing device and moving ambient air across the at least one coil via at least one fan assembly under the control of the controller at a time when the ambient air is cooler than the heat transferring fluid.

7. The method of claim 1 wherein the second assembly includes a second heat spreader and the step of thermally-coupling the second assembly to the second, opposing side of said sample-holding device includes the step of thermally-coupling the second assembly, including the controllable second thermo-electric device, the second heat removal device and the second heat spreader to the second, opposing side of said sample-holding device.

8. The method of claim 1 wherein the second assembly includes a second heat spreader, the thermal control subsystem includes a plurality of sample-holding devices in thermal communication with the first and second heat spreaders, and the thermal control subsystem includes first and second pluralities of thermo-electric devices corresponding in number to the plurality of sample-holding devices in respective first and second assemblies, the first and second pluralities of thermo-electric devices being in thermal communication with respective first and second heat spreaders, the method including maintaining adjacent sample-holding devices within ±0.5° C. of one another.

9. The method of claim 1 wherein the second assembly includes a second heat spreader, the thermal control subsystem includes a plurality of sample-holding devices in thermal communication with the first and second heat spreaders, and the thermal control subsystem includes first and second pluralities of thermo-electric devices corresponding in number to the plurality of sample-holding devices in respective first and second assemblies, the first and second pluralities of thermo-electric devices being in thermal communication with respective first and second heat spreaders, the method including the step of controlling the pumping of the heat-transferring fluid within the fluidic circuit, controlling the first and second pluralities of thermo-electric devices and controlling the heat exchanger with the controller to ramp the temperature of the sample-holding device for at least one of heating and cooling at a rate between 1° C. and 10° C. per minute.

* * * * *